(12) United States Patent
Mayer et al.

(10) Patent No.: US 7,008,226 B2
(45) Date of Patent: Mar. 7, 2006

(54) IMPLANT, IN PARTICULAR A DENTAL IMPLANT

(75) Inventors: Jorg Mayer, Niederlenz (CH); Marcel Aeschlimann, Ligerz (CH); Laurent Torriani, Biel (CH)

(73) Assignee: Woodwelding AG, Zurich (CH)

( * ) Notice: Subject to any disclaimer, the term of this patent is extended or adjusted under 35 U.S.C. 154(b) by 302 days.

(21) Appl. No.: 10/417,645

(22) Filed: Apr. 17, 2003

(65) Prior Publication Data

US 2004/0038180 A1 Feb. 26, 2004

(30) Foreign Application Priority Data

Aug. 23, 2002 (CH) .............................................. 1452/02

(51) Int. Cl.
*A61B 17/68* (2006.01)

(52) U.S. Cl. ...................................... 433/173; 433/174
(58) Field of Classification Search ................. 433/172, 433/173, 174, 175, 176
See application file for complete search history.

(56) References Cited

U.S. PATENT DOCUMENTS

| 772,029 | A | 10/1904 | Clark |
| 2,366,274 | A | 1/1945 | Luth et al. |
| 2,458,152 | A | 1/1949 | Eakins |

(Continued)

FOREIGN PATENT DOCUMENTS

| DE | 2418198 | 4/1974 |
| DE | 3045706 | 12/1980 |
| DE | 257797 | 2/1987 |

(Continued)

OTHER PUBLICATIONS

U.S. Appl. No. 10/415,454, filed Aug. 27, 2003, Aeschlimann et al.

U.S. Appl. No. 10/661,692, filed Sep. 12, 2003, Mayer et al.
Reader's Digest Complete Do–it–Yourself Manual (p. 69).
The Simon and Schuster Complete Guide to Home Repair and Maintenance (p. 45).

(Continued)

*Primary Examiner*—Cary E. O'Connor
*Assistant Examiner*—Candice C. Stokes
(74) *Attorney, Agent, or Firm*—Rankin, Hill, Porter & Clark LLP

(57) ABSTRACT

Am implant (1), in particular a dental implant, comprises surface regions (4) of a first type which have osseo-integrative, inflammation-inhibiting, infection-combating and/or growth-promoting properties, and surface regions (8) of a second type which consist of a material which is liquefiable by mechanical oscillations. The implant is positioned in an opening of e.g. a jawbone and then mechanical oscillations, e.g. ultrasound is applied to it while it is pressed against the jawbone. The liquefiable material is such liquefied at least partly and is pressed into unevennesses and pores of the surrounding bone tissue where after resolidification it forms a positive-fit connection between the implant and the bone tissue. The surface regions of the two types are arranged and dimensioned such that, during implantation, the liquefied material does not flow or flows only very little over the surface regions of the first type such enabling the biologically integrative properties of these surface regions to start acting directly after implantation. The dental implant comprises a central implant part (1) which for example consists of titanium, which comprises at its proximal end a fixation location (3) or an artificial tooth crown, and which forms the surface regions (4) of the first type. Furthermore the implant comprises a peripheral implant part (2) which consists of a liquefiable material and forms the surface regions (8) of the second type. The dental implant achieves with the help of the positive fit a very good (primary) stability which is later taken over by the (secondary) stability of the osseointegration when resorbable liquefiable materials are used or which is supplemented by the stability of osseointegration when non-resorbable liquefiable materials are used.

16 Claims, 3 Drawing Sheets

U.S. PATENT DOCUMENTS

| | | |
|---|---|---|
| 2,510,693 A | 6/1950 | Green |
| 2,942,748 A | 6/1960 | Anderson |
| 3,481,803 A | 12/1969 | Hewitt |
| 3,499,222 A | 3/1970 | Linkow et al. |
| 3,612,803 A | 10/1971 | Klaas |
| 3,723,215 A | 3/1973 | Kessler |
| 3,814,353 A | 6/1974 | Balamuth et al. |
| 3,919,775 A | 11/1975 | Malmin |
| 4,032,803 A | 6/1977 | Durr et al. |
| 4,100,954 A | 7/1978 | Muller et al. |
| 4,130,751 A | 12/1978 | Gordon |
| 4,248,232 A | 2/1981 | Engelbrecht et al. |
| 4,328,108 A | 5/1982 | Deeken |
| 4,360,343 A | 11/1982 | Hussein |
| 4,482,795 A | 11/1984 | Hinden |
| 4,525,147 A | 6/1985 | Pitz et al. |
| 4,566,138 A | 1/1986 | Lewis et al. |
| 4,675,972 A | 6/1987 | Bappert et al. |
| 4,717,302 A | 1/1988 | Adams et al. |
| 4,761,871 A | 8/1988 | O'Connor et al. |
| 5,004,422 A | 4/1991 | Propper |
| 5,019,083 A | 5/1991 | Klapper et al. |
| 5,037,442 A | 8/1991 | Wintermantel et al. |
| 5,125,442 A | 6/1992 | Hendrickson |
| 5,163,960 A | 11/1992 | Bonutti |
| 5,167,619 A | 12/1992 | Wuchinich |
| 5,171,148 A | 12/1992 | Wasserman et al. |
| 5,244,933 A | 9/1993 | Eidenbenz et al. |
| 5,271,785 A | 12/1993 | Devine |
| 5,308,205 A | 5/1994 | Lautenschlager |
| 5,393,559 A | 2/1995 | Shoesmith et al. |
| 5,413,578 A | 5/1995 | Zahedi |
| 5,426,341 A | 6/1995 | Bory et al. |
| 5,447,592 A | 9/1995 | Berce et al. |
| 5,547,325 A | 8/1996 | Tucker et al. |
| 5,562,450 A | 10/1996 | Gieloff et al. |
| 5,589,015 A | 12/1996 | Fusco et al. |
| 5,593,425 A | 1/1997 | Bonutti et al. |
| 5,709,823 A | 1/1998 | Hahn |
| 5,735,875 A | 4/1998 | Bonutti et al. |
| 5,752,831 A | 5/1998 | Padros-Fradera |
| 5,766,009 A | 6/1998 | Jeffcoat |
| 5,772,359 A | 6/1998 | Marty |
| 5,780,536 A | 7/1998 | Yokoyama et al. |
| 5,785,476 A | 7/1998 | McDonnell |
| 5,803,736 A | 9/1998 | Merritt, Jr. |
| 5,840,154 A | 11/1998 | Wittmaier |
| 5,871,514 A | 2/1999 | Wiklund et al. |
| 5,871,515 A | 2/1999 | Wiklund et al. |
| 5,897,578 A | 4/1999 | Wiklund et al. |
| 5,919,215 A | 7/1999 | Wiklund et al. |
| 5,941,901 A | 8/1999 | Egan |
| 5,964,764 A | 10/1999 | West, Jr. et al. |
| 5,993,458 A | 11/1999 | Vaitekunas et al. |
| 5,993,477 A | 11/1999 | Vaitekunas et al. |
| 6,007,539 A | 12/1999 | Kirsch et al. |
| 6,039,568 A | 3/2000 | Hinds |
| 6,056,751 A | 5/2000 | Fenton, Jr. |
| 6,059,817 A | 5/2000 | Bonutti et al. |
| 6,068,482 A | 5/2000 | Snow |
| 6,080,161 A | 6/2000 | Eaves, III et al. |
| 6,099,313 A | 8/2000 | Dorken et al. |
| 6,132,214 A | 10/2000 | Suhonen et al. |
| 6,139,320 A | 10/2000 | Hahn |
| 6,141,874 A | 11/2000 | Olsen |
| 6,193,516 B1 | 2/2001 | Story |
| 6,224,373 B1 | 5/2001 | Lee et al. |
| 6,273,717 B1 | 8/2001 | Hahn et al. |
| 6,332,885 B1 | 12/2001 | Martella |
| 6,545,390 B1 | 4/2003 | Hahn et al. |
| 6,592,609 B1 | 7/2003 | Bonutti |
| 6,635,073 B1 | 10/2003 | Bonutti |
| 2002/0044753 A1 | 4/2002 | Nagayama et al. |
| 2002/0077662 A1 | 6/2002 | Bonutti et al. |
| 2003/0118518 A1 | 6/2003 | Hahn et al. |

FOREIGN PATENT DOCUMENTS

| | | |
|---|---|---|
| DE | 3723643 A1 | 7/1987 |
| DE | 3828340 | 8/1988 |
| DE | 3919274 C1 | 6/1989 |
| DE | 9012044.2 | 8/1990 |
| DE | 9012548.7 | 9/1990 |
| DE | 4100636 A1 | 1/1991 |
| DE | 4209191 A1 | 3/1992 |
| DE | 4328108 | 8/1993 |
| DE | 0317757.7 | 11/1993 |
| DE | 19735103 A1 | 8/1997 |
| DE | 19741087 | 9/1997 |
| DE | 19916158 A1 | 4/1999 |
| DE | 19916160 A1 | 4/1999 |
| DE | 20113692 U1 | 8/2001 |
| EP | 0268957 | 6/1988 |
| EP | 0415615 | 8/1990 |
| EP | 0451932 A1 | 4/1991 |
| EP | 0534078 A1 | 7/1992 |
| EP | 0617935 | 10/1994 |
| EP | 1044655 | 3/2000 |
| EP | 1044656 A1 | 10/2000 |
| EP | 1184006 | 3/2002 |
| EP | 1 184 006 A2 | 3/2002 |
| EP | 1199049 | 4/2002 |
| FR | 1164445 | 1/1957 |
| FR | 1407582 | 9/1964 |
| FR | 1495999 | 10/1966 |
| FR | 2205402 | 11/1973 |
| FR | 2455502 | 5/1979 |
| FR | 2615786 | 5/1987 |
| FR | 0269476 | 10/1987 |
| GB | 762906 | 12/1956 |
| GB | 1203305 | 8/1970 |
| GB | 2061183 | 5/1981 |
| GB | 2277448 | 11/1994 |
| GB | 2324470 | 10/1998 |
| JP | 55121024 | 9/1980 |
| JP | 56139918 | 10/1981 |
| JP | 61104817 | 5/1986 |
| JP | 05245941 | 9/1993 |
| JP | 07222752 | 8/1995 |
| JP | 07300904 | 11/1995 |
| JP | 10323351 A1 | 12/1998 |
| WO | WO 88/03391 | 5/1988 |
| WO | WO 91/03211 | 3/1991 |
| WO | WO 94/18373 | 8/1994 |
| WO | WO 96/01377 | 1/1996 |
| WO | WO 96/37163 | 11/1996 |
| WO | WO 98/42988 | 10/1998 |
| WO | WO 01/09445 | 2/2001 |
| WO | WO 02/069817 | 3/2002 |
| WO | WO 02/38070 A1 | 5/2002 |
| WO | WO 02/087459 | 11/2002 |

OTHER PUBLICATIONS

"Linear Vibration Welding of Non Metallic Components", Welding & Metal Fabrication, May 1989, pp. 152–154.

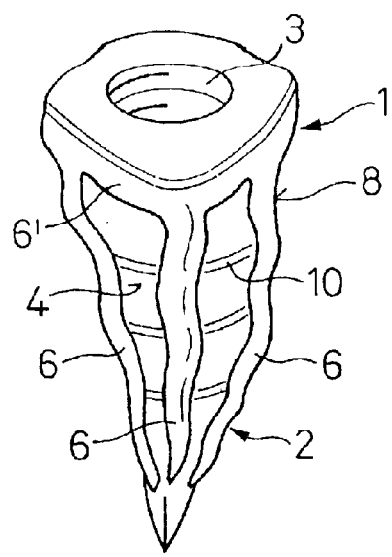
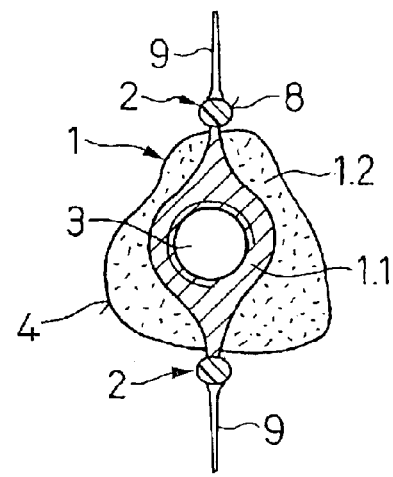
Fig. 3
Fig. 4
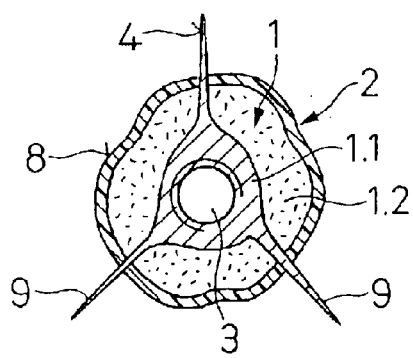
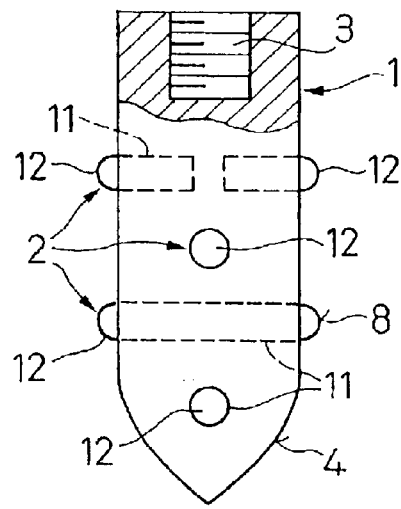
Fig. 5
Fig. 6
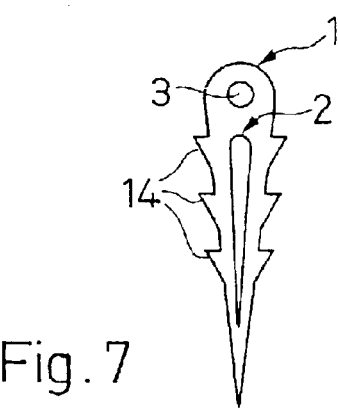
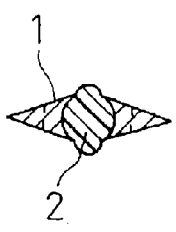
Fig. 7
Fig. 8

IMPLANT, IN PARTICULAR A DENTAL IMPLANT

BACKGROUND OF THE INVENTION

Field of the Invention

The invention is in the field of medical technology and relates to an implant which is suitable for being implanted in bone issue. More particularly, the implant is a dental implant, which, assuming the function of a natural tooth root, is implanted into a jawbone. For purposes of fastening an artificial tooth crown, a bridge or a tooth prosthesis, the implant comprises at its proximal end a fixation location, which after implantation, is located in the region of the bone surface. The dental implant may represent a complete tooth replacement, i.e., the implant may also have a crown region in addition to a root region to be implanted.

According to the state of the art, the fixation of tooth replacement structures (individual teeth, groups of teeth, part-prostheses or complete prostheses) using the above mentioned dental implants with fixation locations is accomplished in the steps described below. After removal of the natural tooth root one waits until naturally regenerated bone tissue fills the opening in the jawbone. Then, in the region of the regenerated bone tissue, an opening adapted to the implant is created. The implant is positioned in the opening, wherein the opening is deep enough for housing the complete implant, which therefore does not protrude beyond the opening. An inner thread defining the fixation location at the end face of the implant is closed with a cover screw. The gum is closed over the cover screw and then one waits until the bone tissue has ingrown with the implant and thereby has a stability (secondary stability) sufficient for the expected loading. Then, in a further step, the gum is opened over the implant and the cover screw is replaced by a distancer, wherein the distancer projects beyond the gum. Only when the gum around the distancer is healed is the tooth replacement structure fastened on the implant. The foregoing described procedure entails a treatment duration of 12 to 18 months for the patient, of which two to three months consists of the time between implantation and a point in time at which the bone tissue has grown around the implant, or the implant is ingrown in the bone tissue, such that the implant has sufficient stability for loading.

The first waiting period (regeneration of bone issue in an opening in the jawbone) may be avoided or shortened if implants are used having a shape adapted as exactly as possible to the original opening, as for example described in U.S. Pat. No. 6,132,214 (Suhonen et al.).

The dental implants according to the state of the art usually consist of pure titanium or of a titanium alloy. These materials exhibit a very good biological compatibility and there are various surface designs known which improve osseointegration. Very often the implants also comprise macroscopic structures that permit the bone issue to grow into or through the implant. However, the stability of these known dental implants is only adequate for full loading after complete osseointegration, i.e., only when they are intimately grown around by bone tissue or ingrown with the bone issue or intergrown with bone issue (secondary stability). In osteoporotic or soft bone, as well as in poorly regenerating bone tissue (for example in older patients), it may not be possible to achieve sufficient implant stability.

The primary stability of the above-described dental implants, i.e. their stability directly after implantation, is greatly limited. For this reason, the above mentioned waiting time is added between implantation and further build up. The primary stability of the mentioned implants varies according to implant form, but in no case is it sufficient for full loading. Pin-like implants with a thread are restrictively loadable by tension and compression and possibly transverse forces, in particular when implanted such that at least one thread convolution lies in the region of the cortical part of the bone. They cannot be loaded by torsion. Implants that do not have a round cross section, i.e. that are adapted to a natural tooth root, are more stable when loaded by torsion, but less stable when loaded by tension. The same applies to plate-like implants, which may also comprise a plurality of fixation locations.

Dental implants implanted according to established techniques cannot be loaded directly after implantation since their primary stability is insufficient. Therefore, early loading would result in movements between implant and bone issue great enough for impeding or even preventing osseointegration. However, immediate loading of implants is not only desirable in order to shorten the treatment duration, but also to avoid atrophy of the jawbone due to non-loading, i.e. to promote osseointegration by way of micro-movements (not exceeding a physiological measure) between implant and bone tissue that can only be achieved by loading a stable implant.

The primary stability, in particular the ability to be loaded in tension is increased for pin-like implants according to the state of the art by way of a suitably formed threads (U.S. Pat. No. 3,499,222), by spread-out elements (e.g. U.S. Pat. No. 5,766,009, EP-1184006) or by collar-like elements. Anchor-like implants in particular used for fastening wires are equipped with barb-like surface structures (U.S. Pat. No. 4,360,343) for increasing the primary and secondary stability. However, these improvements do not permit loading of the implants directly after implantation.

SUMMARY OF THE INVENTION

It is therefore the object of the invention to provide an implant suitable for implantation in bone tissue, in particular a dental implant, wherein the implant has a primary stability that is relevantly improved with respect to similar implants according to the state of the art in a manner, such that the implant can be loaded immediately after implantation, or at least significantly earlier after implantation than known implants. Furthermore, the implant according to the invention is to have properties regarding osseointegration such that the above mentioned positive effects on osseointegration effected by early loading can be fully exploited, and at the same time full osseointegration compared with known implants is reduced or delayed to at the most a very low degree. Furthermore, neither the implant according to the invention, nor its implantation is to be significantly more complicated than is the case for implants according to the state of the art.

The surfaces of the implant according to the invention that are to contact the bone tissue or that are to be grown around by bone tissue or that are to be intergrown by bone tissue comprise regions of a first type and regions of a second type. The regions of the first type have (in a known manner) osseointegrative, inflammation-suppressing, infection-combating, growth-promoting and/or other properties having a positive effect on biological integration of the implant in the vital issue. The regions of the second type are designed for creating an improved primary stability.

The surface regions of the first type are for example biologically compatible surfaces (e.g. of titanium) and may further comprise macroscopic structures suitable for ingrowth of bone tissue, porosities, coatings of compounds containing calcium phosphate, surface modifications by phosphonates and/or gels or polymers containing growth factors. The surface regions of the second type comprise a material which is able to be liquefied by way of mechanical oscillation, e.g. a material behaving in a thermoplastic manner (thermoplastic material or composite material with a thermoplastic component) or a thixotropic cement, wherein this material is liquefied on implantation by way of mechanical oscillation, e.g. ultrasound, and is pressed into irregularities or pores of the bone tissue surrounding the implant. The implant, as the case may be, is equipped in a manner such that the surface regions of the second type are created on implantation only, whether it is by combination of various implant parts by a surgeon or a dental surgeon, or by squeezing out the liquefiable material from the inside of the implant to its outer surface on implantation.

In order for the liquefied material of the surface regions of the second type to be pressed into the bone tissue, the surface regions of the second type are arranged in a manner such that they come into contact with the bone tissue on positioning the implant in the bone. This means the surface regions of the second type project, for example, at least locally beyond the surface regions of the first type, or they are located at implant edges, projections, etc. The surface regions of the two types are dimensioned and arranged in a manner such that the liquefied material of the surface regions of the second type does not spread, or only spreads as little as possible to the surface regions of the first type. This guarantees that the properties of the first type regions that are advantageous for implant integration in the vital tissue are not reduced or are reduced only to a very small, clinically acceptable degree. For implants that are moved relative to the bone tissue in an implantation direction during implantation, this is achieved by an arrangement of the two types of surface regions next to one another and parallel to the implantation direction.

In the same way as known implants, the implant according to the invention is implanted in an opening specifically created for the implant possibly in prior regenerated bone tissue e.g. of the jawbone, wherein this opening may accommodate the whole implant (root region) or wherein the implant in a self-cutting manner may be forced deeper into the bone tissue than the opening. The opening, for example, may only concern the cortical bone layer or, with a suitable design of the implant, may be completely omitted. The implant according to the invention may also have a shape adapted to the shape of a removed, natural tooth root and like another replica may be directly implanted into the opening caused by removal of a natural tooth root.

The implant according to the invention, being a dental implant has, for example, the shape of a pin or a natural tooth root and, at its proximal end, comprises a fixation location (e.g. pocket hole with an inner thread or location at which the dental surgeon may create such a pocket hole) or an artificial crown region. At its distal end, the implant may be formed to have a chisel-shape and/or be provided with lateral self-cutting structures. Furthermore, the implant may be plate-shaped, disk-shaped or blade-shaped and comprise one or more fixation locations, or it may have the shape of an anchor on which, for example, a wire can be fastened. The implant according to the invention is of one piece and comprises the above-defined, different surface regions which for example consist of different materials, or it is two-piece or multi-piece, wherein the dental surgeon combines two or more parts of various materials to form the implant.

For implantation, such a dental implant is positioned in the opening in the jawbone or, as the case may be, on the jawbone, and then mechanical oscillation is applied to it, such as ultrasound, and simultaneously it is pressed against the jawbone. This causes at least part of the liquefiable material to be liquefied and pressed into pores and surface irregularities of the surrounding bone tissue, where after solidification it forms a positive-fit connection between the implant and the surrounding bone tissue. According to this embodiment, the implant is, at the same time as liquefaction, advanced in the bone issue (implantation direction).

For applying mechanical oscillation to the positioned implant, the sonotrode of an ultrasound apparatus is, for example, placed onto the proximal end of the implant. Experiments show that good results are achieved with a power of 2 to 20 W per square millimeter active surface. The frequency of the oscillations is between 2 and 200 kHz.

Implants according to the invention may comprise a central implant part of metal, ceramics or of a composite material and a peripheral implant part of the liquefiable material, such as a material with thermoplastic properties. The liquefiable material may also be placed on the inside of a hollow, central implant part, wherein the walls of the central implant part have through openings, through which the liquefied material is pressed under the influence of the mechanical oscillation, thereby forming surface regions of the second type on the outside of the walls. The implant parts may be connected to one another by the manufacturer or the surgeon directly before or during implantation.

The implant may also consist of only a single material that is able to fulfil the demands of mechanical strength of the implant and the fixation location and the demands set by the biological integration, as well as the demand of being liquefiable by mechanical oscillation. As the case may be, in various regions of the implant, the single material may be filled to varying degrees (e.g. with fibres, whiskers or particles), or it may be filled with different materials in different regions. In this case as well, a suitable design of the surface regions to be integrated in the bone issue must be provided to ensure that the surface regions of the second type (liquefied material) primarily comes into contact with the bone tissue and that the liquefied material is not carried onto the surface regions of the first type upon implantation.

The liquefiable material is advantageously biologically degradable (resorbable) so that the stability (primary stability) function of the positive fit between the implant and the bone issue is gradually taken over by the stability (secondary stability) function of the osseointegration. In particular, in the case of osteoporotic bone tissue or poorly regenerating bone tissue, it may be advantageous to permanently retain the primary stabilization as a supplement to the secondary stabilization, i.e. to use a non-resorbable, liquefiable material, which may be designed itself for good biological integration (secondary osseointegration).

Resorbable polymers based on lactic acid and/or glycolic acid (PLA, PLLA, PGA, PLGA etc.) or polyhydroxyalkanoates (PHA), polycaprolactones (PCL), polysaccharides, polydioxanones (PD), polyanhydrides, polypeptides or corresponding copolymers or blended polymers or composite materials containing the mentioned polymers as components are suitable as resorbable liquefiable materials. Thermoplasts, such as for example polyolefins, polyacrylates, polymetacrylates, polycarbonates, polyamides, polyesters, polyurethanes, polysulphones, polyaryl ketones, polyimides, polyphenyl sulphides or liquid crystal polymers (LCPS), polyacetals, halogenated polymers, in particular halogenated polyoelefins, polyphenylene sulphides, polysulphones, polyethers or corresponding copolymers or blended polymers or composite materials containing the mentioned polymers as components are suitable as non-resorbable polymers. Applicable thixotropic systems are resorbable, partly resorbable or non-resorbable polymeric, ceramic or hydraulic cements (e.g. Norian® of Synthes or Sufix® of Centerpulse).

The design of the implant and the selection of the liquefiable material are to be matched to one another in a manner such that the strength of the positive fit is sufficient for the expected loading, and in a manner such that liquefaction entails a reasonable, that is to say, a low as possible heat release. If liquefiable materials with a relatively high softening temperature are used, it is advantageous to ensure that the implant as a whole (including liquefiable material) conducts the mechanical oscillations as a resonator so that the liquefiable material is liquefied in the surface regions of the second type only very locally, i.e. only in regions of suitably provided energy directors. In this manner, the released quantity of heat can be kept to within an acceptable scope. When using a material with a relatively low softening temperature or a material being liquefiable without the release of heat (e.g. thixotropic cements) and/or when using a thin-walled design of the parts of the liquefiable material, liquefaction may also be effected in the inside of the liquefiable material (by large damping of the exciting oscillation) or at contact locations between the central and peripheral implant part.

The heat burden on the issue during implantation may be reduced even further by designing the central implant part to comprise materials with a large heat-conducting capability and/or a large thermal capacity (e.g. silicon carbide) and, as the case may be, to comprise cooling channels through which a cooling medium may flow.

BRIEF DESCRIPTION OF THE DRAWINGS

Exemplary embodiments of the implant according to the invention are described in detail by way of the following Figures. The implants shown in the Figs. and correspondingly described are all dental implants. This does not mean that the invention is restricted to dental implants. The invention also concerns implants that are to be implanted in areas other than jaw bones, where good primary stability combined with unimpaired osseointegration is advantageous and important. Such implants may, for example, be pin shaped implants for stabilizing bone fractures or cracks or for fixing plates or joint prostheses. Of the Figs.:

FIG. 3 shows a second exemplary embodiment of the dental implant according to the invention, the implant comprising a central and a peripheral implant part, wherein the shape of the implant is adapted to an opening caused by removal of a natural tooth root from a jawbone;

FIGS. 4 and 5 show two further embodiments of the dental implant according to the invention, the implant comprising a central and a peripheral implant part, wherein the central implant part is an imitation of a natural tooth root and is designed self-cutting (cross section);

FIG. 6 shows a further essentially pin-like embodiment of a dental implant according to the invention, the implant comprising a central and a peripheral implant part (side view);

FIGS. 7 and 8 show an exemplary embodiment of a dental implant according to the invention the implant being shaped as an anchor (FIG. 7: side view; FIG. 8: cross section;

FIG. 10: plan view); FIG. 12: plan view).

DETAILED DESCRIPTION OF THE PREFERRED EMBODIMENTS

Figure 1:
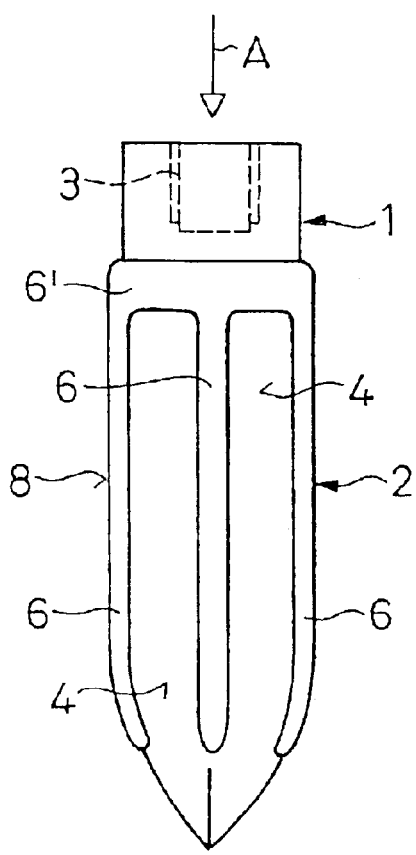
FIGS. 1, 2A, 2B, 2C show three first exemplary embodiments of a pin-like dental implant according to the invention, the implants comprising a central and a peripheral implant part, (FIG. 1: side view, FIGS. 2A to 2C: cross sections)
Figure 2A:
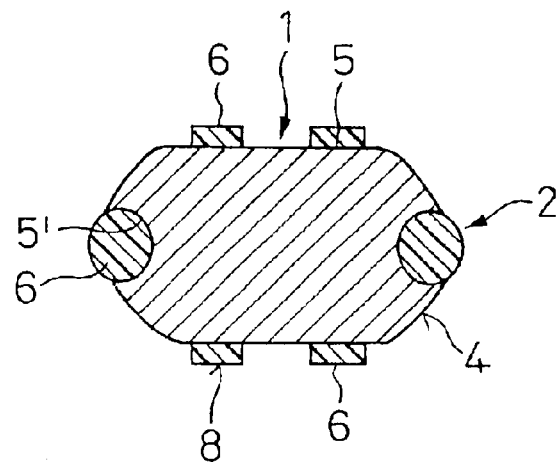
Figure 2B:
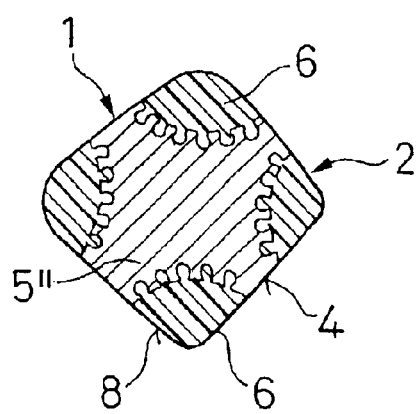

FIGS. 1 and 2A to 2C show an exemplary, pin-like embodiment of the dental implant according to the invention. The dental implant comprises a central implant part 1 and a peripheral implant part 2, wherein the central implant part 1 comprises at its proximal end a fixation location 3 (such as a pocket hole with an inner thread or a location at which the dental surgeon may create such a pocket hole) or an artificial tooth crown. The implant is designed to be chisel-shaped for a self-cutting effect. The implant may also, as illustrated in the cross section according to FIG. 2C, comprise axially extending, self-cutting elements 9. The central implant part 1 comprises surface regions 4 of the first type (e.g. with osseo-integrative, inflammation-inhibiting, infection-combating and/or growth-promoting properties) extending parallel to the implantation direction A. Between the surface regions 4 of the first type, the implant comprises surfaces which are suitable for connection to the peripheral implant part 2. The connection between the peripheral implant part 2 and the central implant part may be an adhesive connection 5 (FIG. 2A), or a material-fit connection, such as individual grooves 5' (FIGS. 2A and 2C) with narrowed opening slots or surfaces 5" with a multitude of openings or grooves (FIG. 2B). The peripheral implant part 2 comprises fingers 6 which, for example, fit into the grooves 5' or onto the surface regions 5" and which form at least one part of the surface regions 8 of the second type.

Figure 2C:
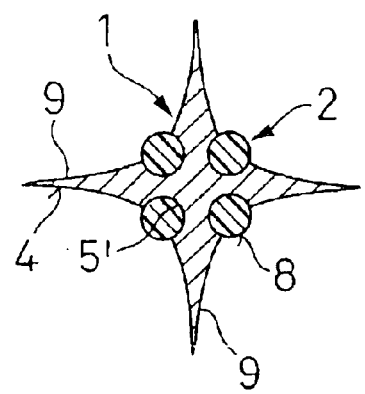

As seen in FIGS. 2A to 2C, the invention does not set any conditions on the cross section of the dental implants, so that this may be selected, depending on the function. Therefore, cross sections other than those shown in the three FIGS. 2A to 2C are conceivable. For example, a central implant part with a round cross-section and fingers 6 seated thereon is shown in FIG. 2A.

The dental implant illustrated in FIG. 2C may, in particular, be driven into the bone tissue (for example) in a largely self-cutting manner. In order to prevent the liquefied material from being driven onto the surface regions 4 of the first type, the surface regions of the first and of the second type (4 and 8) extend next to one another and parallel to the implantation direction A. In the proximal region where the implantation path is short, the fingers 6 may open out into a ring 6' extending around the central implant part 1 and advantageously held in a groove of the central implant part. The ring 6' not only groups the fingers 6 together into a coherent, peripheral implant part 2, which is advantageous for easy connection of the two parts by the dental surgeon, but also constitutes a means for intimate primary stabilization between the implant and the cortical bone tissue, particularly against tension and torsion. Where appropriate, a thread or a similar structure is created in the cortical bone so that the ring 6' can be connected to this relatively compact bone layer by a positive fit.

In order to position an implant in a deeper opening and not be displaced or only slightly displaced during oscillation, the surface regions of the first and second type may be arranged differently. The surface regions 8 of the second type may, instead of forming fingers 6, form a pattern of points or intersecting lines. Thus, the arrangement of the surface regions 8 of the second type is to be adapted to the manner of implantation. Furthermore, the arrangement of the first type surface regions is to be adapted to the primary stability to be achieved by the liquefied material, i.e. the primary stability that cannot be achieved by the implant shape.

The two implant parts 1 and 2 of the dental implants shown in FIGS. 1 and 2A to 2C may be connected to one another by the manufacturer. The peripheral implant part 2 may, for example, be manufactured by injection moulding directly on the central implant part 1. The two implant parts 1 and 2 may also be manufactured separately and later joined together by the dental surgeon just before the implantation. In such a case, it is advantageous to realize the positive-fit or adhesive connection between the two materials during the implantation since the material of the peripheral implant part 2 is liquefied and, for example, is pressed into openings or grooves according to FIG. 2B of the central implant part. For this, it may be necessary to provide the inner side of the peripheral implant part 2 or the corresponding surface of the central implant apart 1 with energy directors.

The advantage of having the dental surgeon join the two implant parts together is that the two parts can be sterilized separately, which would permit different methods to be used that are adapted to the various functionalities of the parts. Joining together the implant parts just before implantation allows the manufacturer to make available a set of central implant parts differing from one another, for example, with respect to length and diameter, and peripheral implant parts differing, for example, with respect to material or finger thickness, so that the dental surgeon may himself put together a suitable implant exactly for the case in question.

FIG. 3 shows a dental implant according to the invention, which in principle, is designed as the implant according to FIG. 1 but takes its shape not from the known pin-like or screw-like implants, but rather from a natural tooth root. Between the surface regions 8 of the second type that are formed by the peripheral implant part 2 (i.e. in the surface regions 4 of the first type), the central implant 1 is provided with structures permitting, like a thread, an improved anchoring in the regenerated bone tissue (secondary stability).

FIGS. 4 and 5 show in cross section two further embodiments of the dental implant according to the invention that are adapted to natural tooth roots and which comprise axially extending, self-cutting elements 9. The central implant part 1 of the two implants consists of a pin part 1.1 with a fixation location 3 or an artificial tooth crown and a body part 1.2. The body part 1.2 is shaped, ex situ, in the sense of a replica, using the removed tooth root, such as described in U.S. Pat. No. 6,132,214 (Suhonen et al.), or, in situ, i.e. in an opening created by removal of a natural tooth root in the jawbone.

The body part 1.2 according to FIG. 4 forms the surface region 4 of the first type (e.g. with osseo-integrative, inflammation-inhibiting, infection-combating and/or growth promoting properties) and consists of an advantageously resorbable or partly resorbable bone replacement material (e.g. calcium phosphate, polylactide, non-resorbable polymer filled with calcium phosphate), or it is a connection system with reinforcing elements. The peripheral implant part 2 is limited to the self-cutting elements 9 into which, for example, pin-like parts of the liquefiable material are introduced.

The body part 1.2 according to FIG. 5 is formed by a relatively thin and flexible (as much as possible) layer of the liquefiable material, i.e. is surrounded by the peripheral implant part 2, which forms the surface of the second type. The axially extending, self-cutting elements 9 comprise the surfaces 4 of the first type. The body part 1.2 consists of a plastic, curable material, such as bone cement, which may be cured by light, ultrasound or heat, and which preferably has thixotropic properties. On introduction into the opening of the jawbone, the body part 1.2 takes the shape of this opening. On applying mechanical oscillations, the liquefiable material of the surface regions of the second type is pressed into pores and irregularities of the surrounding bone tissue, and the body part is adapted to the shape of the opening in the jawbone and is possibly also cured. The liquefiable material is advantageously resorbable so that the primary stability created by the surface regions 8 of the second type is taken over by a secondary stability, which is primarily caused by osseointegration of the body part 1.2 and, after its resorption, by an osseointegration of the pin part 1.1.

The dental implants according to FIGS. 4 and 5 may be implanted in the jawbone essentially directly after removal of a natural tooth root. Thanks to the primary stability achieved by the surface regions 8 of the second type they may also be loaded immediately, thereby causing micro004movements with physiological effects accelerating osseointegration of the shape part 1.2 and later of the pin part 1.1. These dental implants thus shorten the treatment time even more than the implants according to FIGS. 1 to 3.

FIG. 6 shows a further, pin-like embodiment of the dental implant according to the invention. The implant comprises a central implant part 1 and a peripheral implant part 2. The central implant part 1 comprises through openings and/or non-through openings 11 for intergrowth with bone tissue, in which, for example, pins 12 of the liquefiable material are inserted and project beyond the surface of the central implant part 1 and are held firmly by a friction fit. The pins 12 together form the peripheral implant part 2. The ends of the pins projecting out of the openings 11 form the surfaces 8 of the second type.

FIGS. 7 and 8 show in a side view and in cross-section an anchor-like embodiment of the dental implant according to the invention. The fixation location 3 of this embodiment is, for example, formed as an eyelet. The anchor has a per se known shape and comprises a slot running over its length. In the slot, a pin of the liquefiable material (peripheral implant part 2) is arranged with a positive fit. The pin 13 projects on both sides beyond the surface of the anchor. The anchor-like implant, may comprise additional barbs 14 which, on loading in tension, are pressed into the bone tissue, thereby supplementing the positive-fit anchoring by the peripheral implant part 2. However, such barbs or similar retention means are by no means necessary.

The design of the anchor edges as cutter blades simplifies implantation without the use of a suitable opening in the jawbone or in an opening which only concerns the cortical bone.

Figure 9:
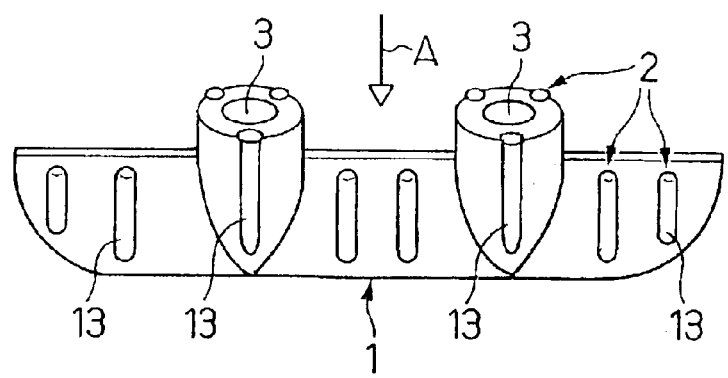
FIGS. 9 and 10 show an exemplary embodiment of a plate-like, disk-like or blade-like dental implant according to the invention, the implant comprising two fixation locations (FIG. 9: side view.
Figure 10:
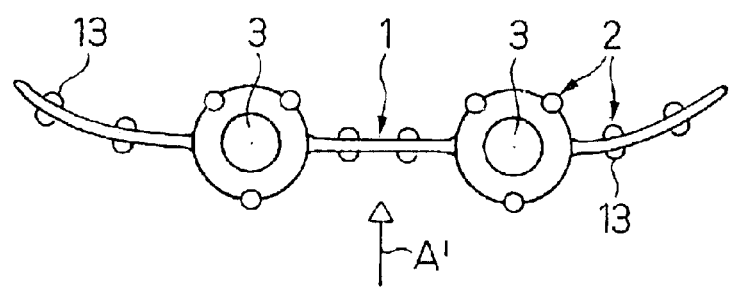

FIGS. 9 and 10 show as a further exemplary embodiment of the dental implant according to the invention, a plate-like, disk-like or blade-like dental implant, which, for example, comprises two fixation locations 3, or two artificial tooth crowns, and whose peripheral implant part 2 consists of a plurality of pin-like parts 13, which are positioned in through openings in the plate, disk or blade, and in the region of the fixation locations in grooves of the central implant part.

The plate-like, disk-like or blade-like dental implants, of which one example is shown in FIGS. 9 and 10, are positioned in the jaw from the jaw ridge in the same manner as pin-like dental implants during application of mechanical oscillation (implantation direction A, FIG. 9). However, they may also be implanted into the jawbone from the side (implantation direction A', FIG. 10). For this type of implantation, a part of the jawbone is removed and re-positioned after implantation.

Figure 11:
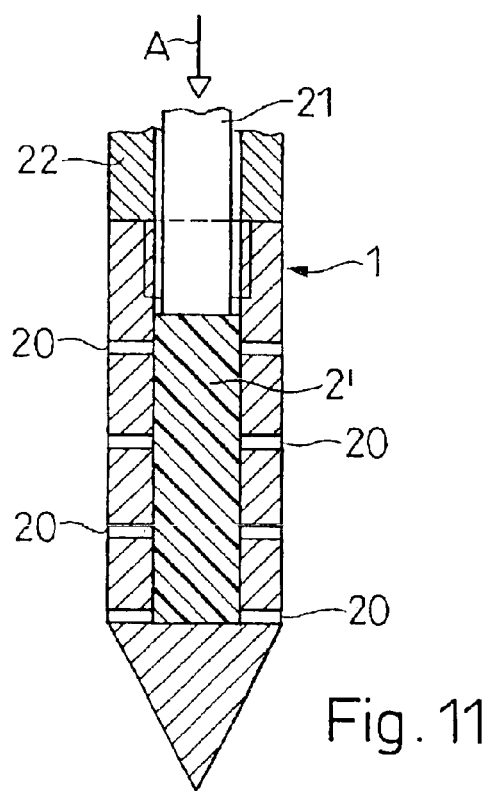
FIGS. 11 and 12 show an exemplary embodiment of a pin-like dental implant according to the invention, the implant comprising a hollow central implant part (FIG. 11: longitudinal section.
Figure 12:
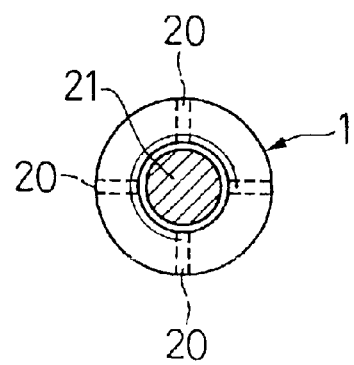

FIGS. 11 and 12 show a further pin-like embodiment of the dental implant according to the invention in a longitudinal section and as a plan view. The central implant part 1 is designed as a sleeve in which the liquefiable material 2' for the peripheral implant part is contained. The sleeve comprises through openings or slots 20, which, for example, are arranged in axial rows or extend axially. The implant is positioned in the opening of the jawbone and an oscillating element 21 (sonotrode of an ultrasound apparatus) is placed onto the material 2' in the inside of the central implant part. The oscillating element 21 applies oscillation to this material and simultaneously presses against the distal implant end. As a result of the oscillations, the material 2' is liquefied and as a result of the pressure, it is pressed through the openings or slots 20 into surface irregularities and pores of the surrounding bone tissue, thereby creating the positive fit for primarily stabilizing the implant.

If the central implant part 1 is provided with a chisel-like, distal end as shown, the implant according to FIGS. 11 and 12 can also be driven into the bone tissue (at least cancellous bone) without the need of an opening. An annular sonotrode 22 is suitable for this. Sonotrode 21 is applied as soon as the implant has reached the predefined position in the jawbone.

In an implant according to FIGS. 9 and 10, the peripheral implant part is actually created only when the implant is positioned in the opening of the jawbone.

The material 2' to be liquefied by way of mechanical oscillation and contained within the central implant part 1 according to FIGS. 11 and 12 preferably has a relatively low softening temperature for reducing the quantity of heat liberated, since a larger quantity of material needs to be liquefied than is the case for the implants according to FIGS. 1 to 10. For this reason, it may be advantageous not to use a thermoplastic material, but instead, to use a highly viscous, polymeric or hydraulic cement having thixotropic properties, which is therefore able to be liquefied with the release of little or no heat. After implantation, such a material is cured, for example, by way of ultraviolet light, heat, mechanical oscillations or simply with time.

When using a thermoplast as a liquefiable material 2' that is to be contained within a central implant part 1, energy directors are arranged on the inner surfaces of the central implant part 1 or on the surfaces of the thermoplast.

The material 2' may be introduced in the central implant part 1 by the manufacturer or by the dental surgeon. It is introduced in any number of individual portions, or it may be pressed using the sonotrode essentially continuously into the central implant part 1.

What is claimed is:

1. An implant for implantation in bone tissue, the implant comprising:
   a surface adapted to come into contact with the bone tissue, said surface comprising surface regions (4) of a first type and surface regions (8) of a second type, wherein the surface regions (8) of the second type comprise a material being liquefiable by mechanical oscillation and wherein the surface regions of the first and second type (4, 8) are dimensioned and arranged in a manner such that the surface regions of the first type remain at least partly free from liquefied material on implantation by mechanical oscillations.

2. The implant according to claim 1, wherein the surface regions (4) of the first type have osseo-integrative, inflammation-inhibiting, infection-combating and/or growth-promoting properties.

3. The implant according to claim 1, wherein the liquefiable material is a material with thermoplastic properties or with thixotropic properties.

4. The implant according to claim 3, wherein the liquefiable material is a polymer based on lactic acid and/or glycolic acid, a polyhydroxy alkanoate, a polycaprolactone, a polysacharide, a polypeptide, a polydioxanone, a polyanhydride, a polyolefin, a polyacrylate, a polymetacrylate, a polycarbonate, a polyamide, a polyester, a polyurethane, a polysulphone, a polyarylketone, a polyimide, a polyphenyl sulphide, a liquid crystal polymer, a polyacetal, a halogenated polymer, in particular a halogenated polyolefin, a polyphenylene sulphide, a polysulphone, or a polyether or a copolymer or blended polymer of the mentioned polymers or a composite material containing one of the mentioned polymers, or a polymeric; ceramic or hydraulic cement.

5. The implant according to claim 1, wherein the implant further comprises a central implant part (1) comprising the surface regions (4) of the first type and a fixation location (3) or an artificial tooth crown.

6. The implant according to claim 5, wherein the central implant part (1) is pin-like, plate-like, disk-like or blade-like or anchor-like or that it is adapted to the shape of a natural tooth root.

7. The implant according to claim 5, wherein the central implant part (1) consists at least partly of a metal, a metal alloy, a ceramic material or a composite material.

8. The implant according to claim 5, wherein the central implant part (1) comprises self-cutting elements.

9. The implant according to claim 5, wherein the surface regions (8) of the second type are formed by a peripheral implant part (2) which is arranged at least partly on the outside of the central implant part (1) and which consists of the liquefiable material, and wherein the surface regions (8) of the second type at least locally project beyond the surface regions (4) of the first type.

10. The implant according to claim 9, wherein the surface regions (4, 8) of the first and second type are arranged next to one another and extending parallel to an implantation direction (A).

11. The implant according to claim 9, wherein the peripheral implant part (2) comprises a ring (6') of the liquefiable material arranged in the region of a proximal implant end, and fingers (6) integrally formed on the ring (6').

12. The implant according to claim 9, wherein the peripheral implant part (2) comprises a plurality of pins (12, 13) which are arranged in through openings or non-through openings of the central implant part (2) and project beyond the central implant part (1).

13. The implant according to claim 9, wherein the central implant part (1) comprises a pin part (1.1) with a fixation location (3) or with an artificial tooth crown, and a body part (1.2) at least partly surrounding the pin part (1.1), and wherein the body part (1.2) is shaped according to the shape of a natural tooth root.

14. The implant according to claim 13, wherein the body part (1.2) is formed ex situ, consists of a rigid material and forms the surface regions (4) of the first type.

15. The implant according to claim 13, wherein the body part (1.2) consists of a material deformable in situ and is surrounded by a flexible layer of the liquefiable material and wherein the surface regions (4) of the first type are formed by parts of the pin part (1.1) which are not surrounded by the body part (1.2).

16. The implant according to claim 5, wherein the liquefiable material (2') is contained within the central implant part (1) being sleeve-shaped and wherein the sleeve-shaped central implant part (2) is designed for pressing out the liquefiable material (2') between the surface regions (4) of the first type.

* * * * *